(12) United States Patent
Stanton et al.

(10) Patent No.: US 11,452,835 B2
(45) Date of Patent: Sep. 27, 2022

(54) APPARATUS AND METHOD FOR HUMIDITY CONDITIONING SAMPLE GAS OF A PATIENT BREATHING CIRCUIT AFFILIATED WITH A VENTILATOR AND/OR NITRIC OXIDE DELIVERY SYSTEM

(71) Applicant: Mallinckrodt Pharmaceuticals Ireland Limited, Dublin (IE)

(72) Inventors: John P. Stanton, Madison, WI (US); John V. Berndt, Oregon, WI (US)

(73) Assignee: Mallinckrodt Pharmaceuticals Ireland Limited, Dublin (IE)

(*) Notice: Subject to any disclaimer, the term of this patent is extended or adjusted under 35 U.S.C. 154(b) by 335 days.

(21) Appl. No.: 16/665,353

(22) Filed: Oct. 28, 2019

(65) Prior Publication Data

US 2020/0061328 A1 Feb. 27, 2020

Related U.S. Application Data

(62) Division of application No. 15/459,060, filed on Mar. 15, 2017, now Pat. No. 10,485,945.

(Continued)

(51) Int. Cl.
*A61M 16/10* (2006.01)
*A61B 5/097* (2006.01)
(Continued)

(52) U.S. Cl.
CPC ......... *A61M 16/1005* (2014.02); *A61B 5/097* (2013.01); *A61K 33/00* (2013.01); *A61M 16/085* (2014.02); *A61M 16/12* (2013.01); *A61M 16/16* (2013.01); *B01D 53/268* (2013.01); *B01D 71/36* (2013.01); *G01N 33/0011* (2013.01); *G01N 33/0036* (2013.01); *G01N 33/15* (2013.01); *A61M 16/14* (2013.01); *A61M 16/202* (2014.02); *A61M 2016/0039* (2013.01); *A61M 2016/102* (2013.01); *A61M 2016/1035* (2013.01); *A61M 2202/0275* (2013.01); *A61M 2205/02* (2013.01)

(58) Field of Classification Search
CPC ............ A61M 16/1005; A61M 16/085; A61M 16/12; A61M 16/16; A61M 16/122; A61M 16/125; A61M 16/127; A61M 16/142; A61M 16/161; A61M 2016/102; A61M 2016/103; A61B 5/097
See application file for complete search history.

(56) References Cited

U.S. PATENT DOCUMENTS

2007/0246049 A1* 10/2007 Takeda ................ A61M 16/145
128/205.27
2015/0209528 A1* 7/2015 Lee ..................... A61M 15/009
128/200.23

(Continued)

*Primary Examiner* — Dung T Ulsh

(57) ABSTRACT

A therapeutic gas is administered to a patient. A sample gas is drawn from the therapeutic gas supply, and passed through a water-permeable tubular membrane. Concurrently, a section of the water permeable tubular membrane is maintained as a ventilated water permeable tubular membrane, by exposing outer surfaces of the ventilated water permeable tubular membrane to an ambient air flow. The ambient air flow may in some examples be moved over the tubular membrane via forced air such as for example via a fan associated with a housing surrounding the tubular membrane.

19 Claims, 6 Drawing Sheets

Related U.S. Application Data

(60) Provisional application No. 62/331,694, filed on May 4, 2016.

(51) Int. Cl.
| | |
|---|---|
| *A61M 16/08* | (2006.01) |
| *A61K 33/00* | (2006.01) |
| *A61M 16/12* | (2006.01) |
| *A61M 16/16* | (2006.01) |
| *B01D 53/26* | (2006.01) |
| *B01D 71/36* | (2006.01) |
| *G01N 33/00* | (2006.01) |
| *G01N 33/15* | (2006.01) |
| *A61M 16/14* | (2006.01) |
| *A61M 16/20* | (2006.01) |
| *A61M 16/00* | (2006.01) |

(56) References Cited

U.S. PATENT DOCUMENTS

2015/0352306 A1* 12/2015 Scheiner ........... A61M 16/0875
                                                          128/205.25
2018/0250490 A1*  9/2018 Burgess ................ A61M 39/24

* cited by examiner

APPARATUS AND METHOD FOR HUMIDITY CONDITIONING SAMPLE GAS OF A PATIENT BREATHING CIRCUIT AFFILIATED WITH A VENTILATOR AND/OR NITRIC OXIDE DELIVERY SYSTEM

CROSS-REFERENCE TO RELATED APPLICATIONS

This application is a divisional application of U.S. patent application Ser. No. 15/459,060, filed on Mar. 15, 2017, which claims priority to U.S. Patent Application No. 62/331,694, filed on May 4, 2016, the entire contents of which are incorporated herein by reference in their entirety.

FIELD

The present disclosure generally relates to the humidity conditioning of sample gas affiliated with a ventilator and/or nitric oxide delivery system.

BACKGROUND

Many patients benefit from receiving therapeutic gas (e.g., nitric oxide gas) in inspiratory breathing gas flow from a breathing circuit affiliated with a ventilator. The ventilator can be, for example, a constant flow ventilator, variable flow ventilator, high frequency ventilator, bi-level positive airway pressure ventilator or Bi PAP ventilator, etc.). To provide therapeutic gas to the patient, the therapeutic gas may be injected into the inspiratory breathing gas flowing in the breathing circuit. This inhaled therapeutic gas is often provided via a therapeutic gas delivery system as a constant concentration, which is provided based on proportional delivery of the therapeutic gas to the breathing gas. Further, a sampling system (e.g., affiliated with the therapeutic gas delivery system) may continuously draw in the inspiratory breathing gas flow to at least confirm that the desired dose of the therapeutic gas in the inspiratory breathing gas flow is being delivered to the patient. For example, a sample pump may pull in inspiratory flow (e.g., in the vicinity of the patient) to confirm that the desired therapeutic gas concentration is in fact being delivered to the patient in need thereof.

One such therapeutic gas is inhaled nitric oxide (iNO). In many instances iNO is used as a therapeutic gas to produce vasodilatory effect on patients. When inhaled, NO acts to dilate blood vessels in the lungs, improving oxygenation of the blood and reducing pulmonary hypertension. Because of this, nitric oxide is provided in inspiratory breathing gases for patients with various pulmonary pathologies including hypoxic respiratory failure (HRF) and persistent pulmonary hypertension (PPH). The actual administration of iNO is generally carried out by its introduction into the patient as a gas along with other normal inhalation gases, for example, by introducing iNO, from an iNO delivery system, into the inspiratory flow of a patient breathing circuit affiliated with a ventilator.

Separately and/or in conjunction with iNO, patients may receive inspiratory breathing gas flow containing liquid particles (e.g., moisture from humidified air, etc.) and/or other particles. Although this matter in the inspiratory breathing flow may provide additional benefit to the patient, it may interfere with or degrade operation of the sample gas analyzer. For example, the sample gas analyzer itself may work best when it receives sample gas within a given humidity range, and liquid particles as described above may be inconsistent with that range.

One known technique directed at keeping the sample gas at a desired humidity is to use, as part of the pathway of the sample gas before it arrives at the analyzer, a tubing formed of a sulfonated tetrafluoroethylene based fluoropolymer-copolymer, for example, the commercially available Nafion® tubing. Properties of such tubing include a permeability that is very selective to water and that provides rapid transfer through the tubing walls. Provided that the permeability is maintained, such tubing can provide a mechanism operating as follows: if the humidity level of the sample gas passing through the tubing exceeds an acceptable maximum (and assumedly above ambient), some of that excess humidity will permeate out through the tube walls before the sample gas reaches the analyzer. Conversely, if the humidity level of the sample gas passing through the tubing is below the acceptable minimum (and assumedly below ambient), some of the ambient humidity will permeate in through the tube walls and raise the humidity of the sample gas to be within an acceptable range, prior to reaching the analyzer.

However, a conventional arrangement of Nafion tubing can form, over time, a dry external layer, i.e., at its outer wall surface, or dry inner layer at its passage wall surfaces, or both. With subscribing to any particular scientific theory, the inventor believes the mechanism of the drying may be a dehydration of the aqueous sulfonic acid inherent to the Nafion construction. Such dry layers can effectively become an obstruction to the above-described humidity conditioning function. This drying and obstructing layer formation can significantly shorten the operational life of Nafion (and equivalent) tubing type humidity conditioners.

Accordingly, there is a need for a humidity conditioner having the performance that can be obtained with Nafion and, concurrently, a significantly longer operational life than provided by conventional technique Nafion humidity conditioners.

SUMMARY

Aspects of the present disclosure generally relate to apparatuses and methods directed to enhanced performance and extended equipment life in humidity conditioning of sample gas. More specifically some implementations relate to enhancing or controlling the humidity of sample gas affiliated with a ventilator and/or nitric oxide delivery system. Further, some implementations relate to the humidity of sample gas prior to being analyzed by a gas analyzer. Further, some implementations relate to humidity conditioning a sample gas, using Nafion tubing, by passing ambient air over the tubing using a fan or other forced air device. The tubing may be in the form of a coil housed in a housing, with a fan forcing (or blowing) air over the tubing.

Disclosed aspects include a sample gas conditioning apparatus, and the apparatus can include a housing, at least partially defining a chamber, and at least partially defining an air input path into the chamber and an air egress path from the chamber. In an aspect, the sample gas conditioning apparatus can include a fan, connected to the housing, and configured to urge an ambient air flow through the chamber, the ambient air flow entering through the air input path into the chamber, and exiting the chamber through the air egress path. The sample gas conditioning apparatus can include, in an aspect, a sample gas tube having a section that comprises a permeable material. Disclosed aspects include the section being arranged and supported in the chamber in a configuration wherein at least a portion of the section is a ventilated section, ventilated by the ambient air flow through the chamber.

Disclosed aspects also include structure for arranging and supporting the ventilated section in the chamber in a configuration, relative to the ambient air flow through the chamber, that establishes flow parameters of the ambient air flow, in regions adjacent to outer surfaces of the ventilated section, at levels that prevent or significantly retard formation of a skin of dry gas around the outer surface of the ventilated section.

Disclosed aspects also include the sample gas tube having an input end and an output end, and can include the section comprising permeable material providing a passage distance for the sample gas, wherein the passage distance in combination with a flow rate of the sample gas provides, for at least a range of humidity level of sample gas at the input end that is outside of a given acceptable range, a conditioning of the sample gas as it travels the passage distance wherein, at the output end, the humidity level is within the given acceptable range. Disclosed examples include, but are not limited to, an acceptable range that extends from approximately 15% relative humidity to approximately 90% relative humidity.

Disclosed examples include the sample gas tube having an input and an output, and in an aspect the apparatus can further comprise a connection of the input to a conduit, the conduit being configured to deliver a mixture of a mixture gas and a therapeutic gas to a patient. In an aspect, the sample gas tube can be configured to provide passage of a sample of the mixture of the mixture gas and the therapeutic gas to the ventilated section, and to output, at the output, a humidity conditioned sample of the mixture of the mixture gas and the therapeutic gas. In an aspect the therapeutic gas comprises inhaled nitric oxide.

Disclosed aspects include the fan being connected to the housing, in an alignment with the air egress path, and in a configuration that urges a negative pressure in the chamber. In an aspect, the negative pressure can effect an urging of the ambient airflow through the airflow input to the chamber, out through the air egress path, and into the fan.

Disclosed aspects include the water permeable material comprising a sulfonated tetrafluoroethylene based fluoropolymer-copolymer, and include the water permeable material comprising Nafion.

Disclosed aspects also include the tube walls of the ventilated section providing a tubular membrane, formed of the permeable material, and the permeable material transferring water through the tubular membrane, based on First Order Kinetic reaction. In addition, disclosed aspects include the tubular membrane having a start and having an end, and providing a passage length from the start to the end, wherein based at least in part on the passage length the tubular membrane provides, for at least a range of humidity level of the sample gas at the start that is outside of a given acceptable range, a humidity level of the sample gas at the end that is within the given acceptable range.

Disclosed aspects include the ventilated section being a coiled tube section, with windings around a winding axis. Disclosed aspects include the coiled section having a winding turn and, in another aspect, having at least two winding turns.

Disclosed aspects also include a configuration of the air input path, the air egress path, and inner wall surfaces of the housing, relative to the coiled section, that urges the ambient airflow through the chamber according to a flow direction, the flow direction being generally parallel to the winding axis. In addition, disclosed aspects include the winding turns forming a coil winding outer surface, the coil winding outer surface being radially distal from the winding axis, and the chamber being defined, at least in part, by an inner surface of the housing that extends a length along the winding axis and, circumferentially around the winding axis, faces toward the winding axis.

Disclosed aspects include the housing having a housing cap, having a cap perimeter, and that the housing having housing sidewalls that extend, parallel to the winding axis, from the cap perimeter to a housing open end. In addition, disclosed aspects include the housing sidewalls forming sidewall inner surfaces that can face and have a clearance from the coil winding outer surface. Disclosed aspects also include the housing being configured to provide the air egress path as at least a portion of the housing open end area. In addition, disclosed aspects include the housing cap being a vented housing cap, providing a vent into the chamber, and the air inlet path as comprising the vent.

Disclosed aspects include the fan as comprising an electric motor, that can be supported in a fan housing, and a rotor shaft and a rotary fan blade attached to the rotor shaft. In addition, disclosed aspects include the housing being configured with a housing mounting flange at the housing open end, and that the fan housing can be secured to the housing mounting flange, in a configuration where the rotor shaft can be parallel to the winding axis.

Also, disclosed aspects include the fan housing being secured to the mounting flange by an adapter plate, the adapter plate having an adapter plate first face and, opposite and parallel to the adapter plate first face, an adapter plate second face. Described exemplary implementations according to this disclosed aspect include the fan housing being secured, by fan housing mount bolts, to the adapter plate first face, in combination with the housing mounting flange being secured, by housing mount bolts, to the adapter plate second face.

Disclosed aspects include providing a method for verifying therapeutic gas for delivery to a patient, and exemplary operations can include adding a therapeutic gas as a supplement to a mixture gas, and delivering to the patient, though a conduit, the mixture gas supplemented with the therapeutic gas is delivered. In an aspect, operations can include receiving a gas sample from the conduit, through a gas sample line, of the mixture gas supplemented with the therapeutic gas. Disclosed aspects include humidity conditioning the sample gas, by passing the sample gas through a water-permeable tubular membrane, wherein the sample gas leaving the water-permeable tubular membrane is a humidity conditioned sample gas, and analyzing the humidity conditioned sample gas to determine a mixing ratio. Disclosed aspect include, concurrent with passing the sample gas through the water-permeable tubular membrane, maintaining a section of the water permeable tubular membrane as a ventilated water permeable tubular membrane, by operations that include exposing outer surfaces of the ventilated water permeable tubular membrane to an ambient air flow.

In an aspect, the therapeutic gas can comprise inhaled nitric oxide. In an aspect, operations in passing the sample gas through the water-permeable tubular membrane can comprise passing the sample gas through a tubular membrane formed of a sulfonated tetrafluoroethylene based fluoropolymer-copolymer. In another aspect, operations in passing the sample gas through the water-permeable tubular membrane can comprise passing the sample gas through a tubular membrane formed of Nafion. Disclosed aspects include providing a method directed to humidity conditioning a sample gas, and operations can include passing the sample gas through a water-permeable tubular membrane and, concurrent with passing the sample gas through the water-permeable tubular membrane, establishing a section of the water permeable tubular membrane as a ventilated water permeable tubular membrane, by exposing outer surfaces of the ventilated water permeable tubular membrane to an ambient air flow.

Disclosed aspects include, in addition, exposing outer surfaces of the ventilated water permeable tubular membrane to the ambient air flow to provide the ambient airflow with characteristics that can prevent or significantly retard formation of a skin of dry gas around the outer surfaces of the ventilated water permeable tubular membrane.

Also, disclosed aspects include establishing the ventilated water permeable tubular membrane to have a start and an end, and a passage length between the start and the end. Disclosed aspects include the passage length being such that the water permeable tubular membrane provides, for at least a range of humidity level at the start that is outside of a given acceptable range, a humidity of the sample gas at the end within the given acceptable range.

Other features and aspects of the disclosure will be apparent from the following detailed description, the drawings, and the claims.

BRIEF DESCRIPTION OF THE DRAWINGS

The features and advantages of the present disclosure will be more fully understood with reference to the following, detailed description when taken in conjunction with the accompanying figures, wherein.

DETAILED DESCRIPTION

Figure 1:
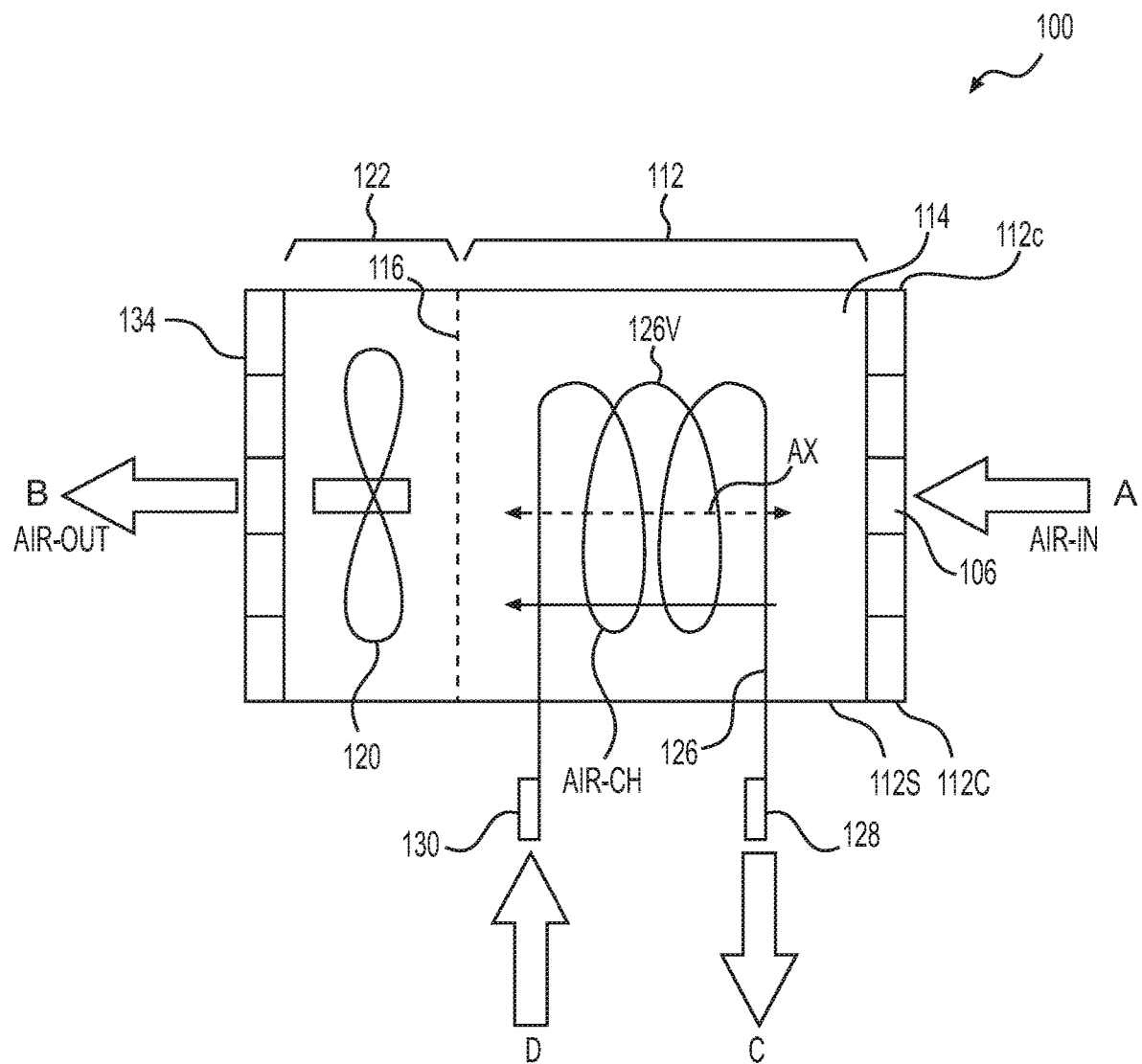
FIG. 1 schematically depicts a gas humidity conditioning apparatus, with an exemplary ambient airflow to humidity transfer tubing, in accordance with one or more aspects.

Generally, aspects of the present disclosure relate to apparatuses and methods to enhance the humidity conditioning of sample gas. More specifically, some implementations relate to enhancing or controlling the humidity of sample gas affiliated with a ventilator and/or nitric oxide delivery system. Further, some implementations relate to the humidity of sample gas prior to its being analyzed by a gas analyzer. Further, some implementations relate to humidity conditioning the sample gas by passing it through a length of Nafion or alternative water permeable tubing and, concurrently, passing ambient air over the tubing using a fan or other forced air device. Various examples in the present disclosure refer to Nafion tubing. Reasons include Nafion being a material that is known in the art. Other reasons include the problems to which this application is directed being known to manifest when Nafion is used for humidity conditioning a sample gas. However, references to Nafion are not intended to limit disclosed systems and methods to Nafion tubing.

For convenience in description, the arbitrary term "selective high permeability material" is hereby introduced and will be introduced to mean: material, including but not limited to sulfonated tetrafluoroethylene based fluoropolymer-copolymer, including Nation, and reasonable equivalents thereto, that exhibits selective, high water permeability, the selectivity and permeability being acceptable for humidifying/de-humidifying sample gas in therapeutic gas delivery systems and having suitable chemical resistance to enable use in therapeutic gas delivery systems. It will also be understood that, except where explicitly stated or made clear from its context to mean otherwise, that the term "Nafion" means: "Nafion or other selective high permeability material."

One sample gas conditioning apparatus according to one or more aspects can include a housing, configured to at least partially define a chamber, and to form, or at least partially define an air input path into the chamber and an air egress path from the chamber. An example sample gas conditioning apparatus according to one or more aspects can also include a fan, connected to the housing, in a configuration such that action of the fan urges an ambient air flow through the chamber, the ambient air flow entering through the air input path into the chamber, and exiting the chamber through the air egress path. An example sample gas conditioning apparatus according to one or more aspects can also include a sample gas tube, having a section that comprises a permeable material. The permeable material can be, for example, Nafion. In an aspect at least a portion of the section can be arranged in the chamber as a ventilated section, the ventilated section being ventilated by the ambient airflow through the chamber. In an aspect, the ventilated section can include a coiled tube section. The coiled tube section can comprise, for example, a winding turn, or least two winding turns, or any integer plurality of winding turns, with or without supplement by partial turns. In an aspect, the winding turns of the coiled tube section can be around a winding axis. In a further aspect, the air input path, air egress path, and the housing can have a joint configuration that urges the ambient air flow through the chamber to have a flow direction, the flow direction being generally parallel to the winding axis. However, in other implementations the tube section may have a coil or winding arrangement that has turns that are other than circular.

It will be understood that in described implementations that include an air input path and flow though the chamber to an air egress path, the structures functioning as the "input air input path" and "air egress path" are only one example. In one alternative implementation, the described fan direction can be reversed, whereupon structure described as input air input path will be the air egress path, and structure described as the air egress path will be the air input path.

In an aspect "sample gas," as used herein, can be a sample gas drawn from a delivered therapeutic gas in the context of delivery of therapeutic gas to patients (e.g., patients receiving breathing gas, with therapeutic gas, from a ventilator circuit). The sample gas, for example, may be removed from an inspiratory limb of a therapeutic gas delivery system to be monitored by a sampling device. Applications can include a filtering of the sample gas prior to being humidity conditioned according to disclosed concepts. Humidity conditioning of sample gas according to disclosed concepts, applied to therapeutic delivery systems may, for example, allow improved accuracy in monitoring what is delivered. Such accuracy can provide improved confirmation of dosing (e.g., nitric oxide concentration, etc.) as well as other parameters (e.g., nitrogen dioxide concentration, oxygen concentration, etc.). As an additional benefit, humidity conditioning of sample gas according to disclosed concepts can provide significantly extended service life of the humidity conditioning tubing. This can reduce costs and make continuous monitoring more feasible.

FIG. 1 shows, in a cross-sectional view, a sample gas conditioning apparatus 100 according to various aspects.

Referring to FIG. 1, apparatus 100 can include a housing 112, which can be configured to at least partially define a chamber 114. The housing 112 can include a cap 112C, and sidewalls 112S. The cap 112C can be integral to the housing 112. Alternatively, the cap 112C can be secured, by adhesive or other means, to a region of the sidewalls 112S. In an aspect, the sidewalls 112S can extend from the cap 112C (right-to-left in the image plane of FIG. 1) to form a housing open-end, identified by the FIG. 1 dotted line labeled 116.

With continuing reference to FIG. 1, the housing 112 may include, for example, a vent 118, as an air input path to the chamber 114. It will be understood that "vent" and "air input path" are not limited to being a single passage. In an aspect, the housing open end 116 can function, for example, as described in greater detail later, as an air passage, opening and/or egress from the chamber 114.

Referring to FIG. 1, in an aspect, the apparatus 100 can include a fan 120, which, according to one aspect, can be connected or mounted to the housing 112. The fan 120 may be connected or mounted, for example, in alignment with, or in another cooperative arrangement with the housing open end 116. The fan 120 can be, for example, an off-the-shelf device, such as readily available from various vendors. The fan 120 can include a frame or housing 122, which is partially visible in the FIG. 1 cross-sectional view. The frame or housing 122 can support a motor-driven rotary fan blade (visible in part but not separately numbered). In one example, the fan 120 can urge an ambient airflow in a direction that, in the FIG. 1 image plane, appears as right-to-left. Accordingly the side of the fan 120 facing toward the housing open end 116 can be termed a "fan input," and the opposite side can be termed a "fan output."

Capacity (e.g., volume per unit time) and electrical power requirements for the fan 120, e.g., voltage and whether AC or DC, are application-specific. Persons of ordinary skill having possession of this disclosure can readily select and implement the fan 120 without undue experimentation.

Upon receiving power, the fan 120 can urge an ambient airflow that can enter the chamber 114 through the air input, e.g., the vent 106, continue through the chamber 114, and exit from the housing open end 116. FIG. 1 labels an example of this ambient airflow according to regions, with "AIR-IN" labeling the ambient airflow entering the chamber 114 through the air input, e.g., the vent 106, "AIR-CH" labeling ambient airflow through the chamber 114, and "AIR-EX" labeling ambient airflow exiting the chamber 114 through the housing open end 116.

Continuing to refer to FIG. 1 the system 100 can include a sample gas tube 126, having an input end (visible in FIG. 1 but not separately numbered) coupled to a tube input coupler 130, and an output end (visible in FIG. 1 but not separately numbered) coupled to a tube output coupler 128. In an aspect, the entire length of the sample gas tube 126, from the input end to the output end, can be formed of Nafion or another selective high permeability material. In one alternative, at least the portion labeled "126V," which will be described as the "ambient air ventilated section 126V," can be formed of Nafion or another selective high permeability material. The example of FIG. 1 may be considered a parallel flow configuration. If the input coupler and output coupler are reversed, as can be the case in some implementations, then the arrangement may be considered a counter-flow arrangement.

In an aspect, the ventilated section 126V can be arranged to be within the ambient airflow AIR-CH. In an arrangement such as illustrated in FIG. 1, the ambient air ventilated section 126V is effectively bathed in the ambient airflow. It will be understood that "within the airflow," in the context of "within the ambient airflow AIR-CH," means exposure to the ambient airflow AIR-CH sufficient to prevent or significantly retard formation of a skin of dry gas around the outer surface of the ambient air ventilated section 126V.

Referring to FIG. 1, the ambient air ventilated section 126V can be configured to include a "coiled tube section" (visible in FIG. 1, but not separately numbered). The coiled tube section can comprise, for example, a winding turn (visible in FIG. 1, but not separately labeled), or any number of winding turns, such the example two (2) winding turns that are visible in FIG. 1. In an aspect, the winding turns of the coiled tube section can be wound around a winding axis, such as the winding axis AX. Further aspects of supporting the coiled tube section within the housing 112 are described in reference to FIGS. 2-5B.

In an aspect, at least the section of the sample gas tube 126 that forms the ambient air tube section 126V can be jacketed by a braided plastic, for example polyester, (not explicitly visible in the figures) to mechanically stabilize and stiffen the material.

Benefits of forming the ambient air ventilated section 126V as a coiled tube section include, for example, providing a greater passage length within a smaller volume. This can provide, among various benefits, a smaller required chamber 114, i.e., smaller housing 112. Another example benefit can be a smaller total flow volume for the ambient airflow AIR-CH.

Regarding the physical length of the ambient air ventilated section 126V, this can be determined, without undue experimentation, by a person of ordinary skill having possession of this disclosure. For example, in various applications, all of the following can be established, ascertained, or given up front: i) the water permeability of the tube walls; ii) the rate of the sample gas (or other gas to be conditioned); iii) the expected range of humidity of the received sample gas (or of the other gas to be conditioned); and iv) the acceptable range for the humidity of the conditioned gas. Identifying all of (i) through (iv), for a given application, can be readily performed by persons of ordinary skill in the art. Therefore, further detailed description is omitted. Upon (i) through (iv), being identified, the physical length of the ambient air ventilated section 126V can be readily determined, for example, by the following guideline in view of this entire disclosure: calculate (or find through simulation)

a physical length such that the gas, after traveling that length, will have humidity that has been raised or lowered (from the maximum and minimum extremes of the input humidity range), to within the acceptable range.

Figure 2:
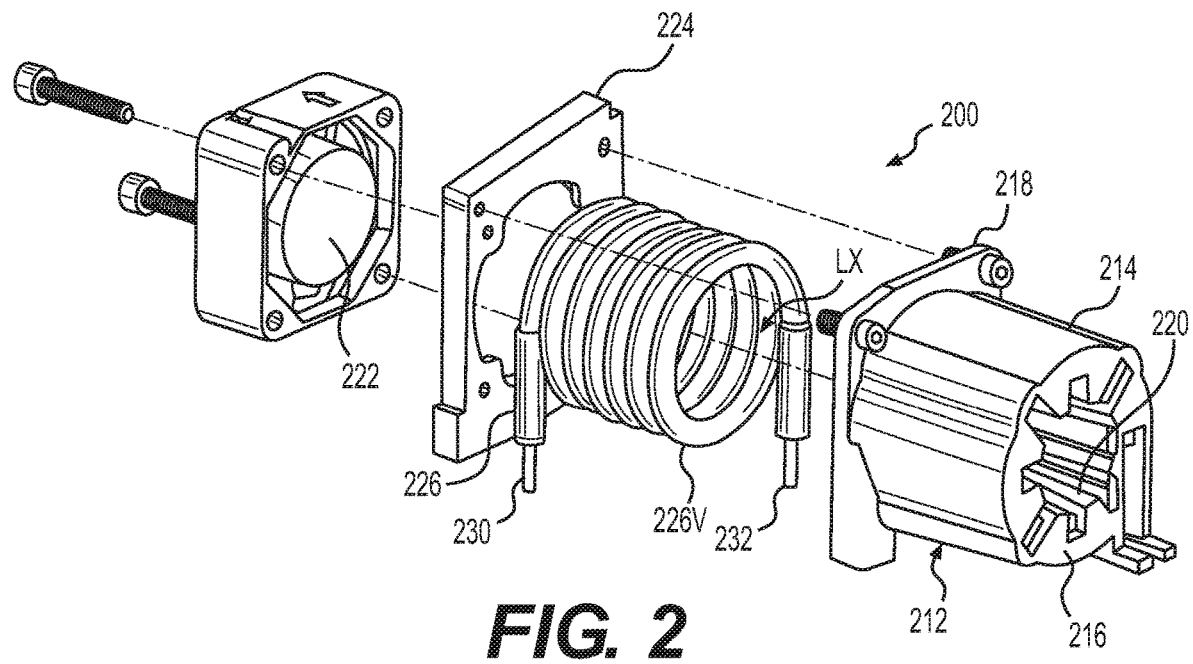
FIG. 2 illustrates a perspective view, depicting in partially exploded form structures in an example gas humidity conditioning apparatus, with an exemplary implementation of ambient airflow to humidity transfer tubing, according to one or more aspects.

FIG. 2 illustrates a perspective view, depicting in partially exploded form structures in one example gas humidity conditioning apparatus 200, with an exemplary ambient airflow, in accordance with one or more aspects. The gas humidity conditioning apparatus 200, with an exemplary implementation of ambient airflow to humidity transfer tubing, will be referred to as "humidity conditioning apparatus" 200.

Referring to FIG. 2, humidity conditioning apparatus 200 can include a housing 212 having sidewalls 214, which can be arranged around and extend parallel to longitudinal axis LX, which will be alternatively referred to as the "winding axis" LX. In an aspect, the housing 212 can include an annular end plate 216. The annular end plate 216 can have an inner perimeter edge (visible in FIG. 2 but not separately labeled) that can be circumferential around the winding axis LX. The annular end plate 216 can also have an outer perimeter edge (visible in FIG. 2 but not separately labeled), which can merge with a peripheral rim (visible in FIG. 2 but not separately labeled) of the housing sidewalls 214. The housing sidewalls 214 can extend from the peripheral rim in a direction parallel to the winding axis LX, to an opposite peripheral rim (visible in FIG. 2 but not separately labeled) that merges with a housing end flange 218. The peripheral rim of the housing 212 that merges with the housing end flange 218 can define an open end (obstructed from view in FIG. 2) of the housing 212.

It will be understood that "merge with," as used in this disclosure, carries no limitation as to structure that effects the merging. For example, "merged with" can include, without limitation, "connected to," "attached to," "fused to" and "molded as respective regions or portions of a single structure."

Continuing to refer to FIG. 2, in an aspect, the housing 212 can include a winding support 220 (partially visible in FIG. 2) that can extend from the inner perimeter edge of the annular end plate 216, in a direction parallel to the winding axis LX. The annular end plate 216, in other words, can support the winding support 220 to extend within the housing sidewalls 214, toward the open end of the housing 212. Various structure and functionalities of the winding support 220 are described in greater detail in reference to FIGS. 5A and 5B.

Continuing to refer to FIG. 2, in an aspect, the gas humidity conditioning apparatus 200 can include a fan 222. The fan 222 can be connected to the housing 212 using, for example, an adapter plate 224. The fan 222 can include a fan housing (visible in FIG. 2 but not separately numbered) that can be bolted to the adapter plate 224. The fan 222 can then be attached to the housing 212 by bolting the adapter plate 224 to the housing end flange 218.

In an aspect, the gas humidity conditioning apparatus 200 can include sample gas tube 226, having a coiled tube section 226V. The coiled tube section 226V can be an implementation of the FIG. 1 ambient air ventilated section 126V. In an aspect, the coiled tube section 226V can be formed of a permeable material, having a high permeability for water. In an implementation, the permeable material can comprise a sulfonated tetrafluoroethylene based fluoropolymer-copolymer. The permeable material, for example, can be Nafion. The sample gas tube 226 can include the tube input end coupled to a tune input coupler 230, and an output end coupled to a tube output coupler 232.

In an aspect, at least the section of the sample gas tube 226 that forms the coiled tube section 226V can be jacketed by a braided plastic, for example polyester, (not explicitly visible in the figures) to mechanically stabilize and stiffen the material.

Figure 3:
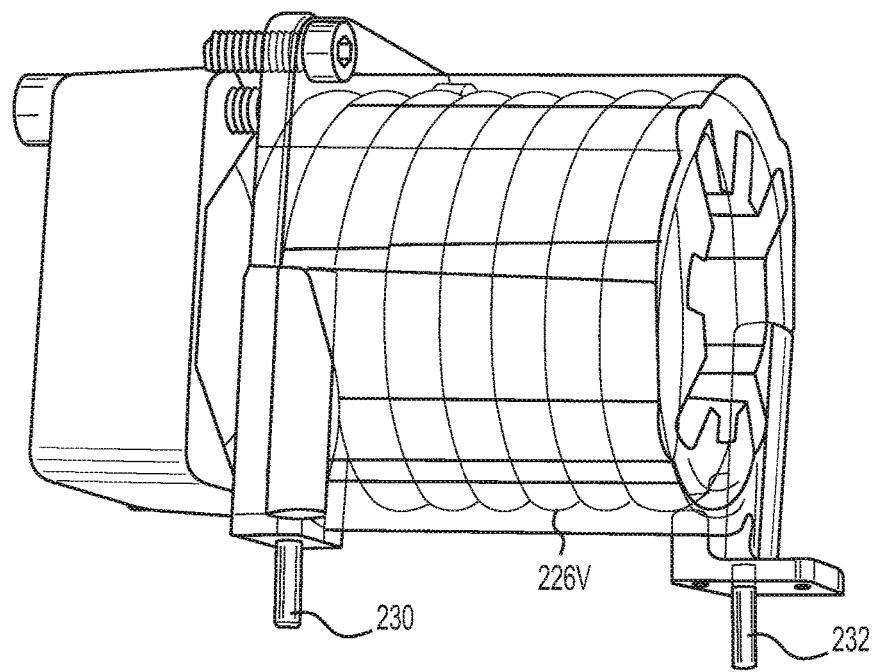
FIG. 3 illustratively depicts a perspective view of the FIG. 2 apparatus, in a construct showing an assembled form.

FIG. 3 illustratively depicts a perspective view of the gas humidity conditioning 200 apparatus, in a construct showing an assembled form, with the housing sidewalls 214 rendered transparent. Referring to FIG. 3, the arrangement of the coiled tube section 226V of the sample gas tube 226 is partially visible.

Figure 4:
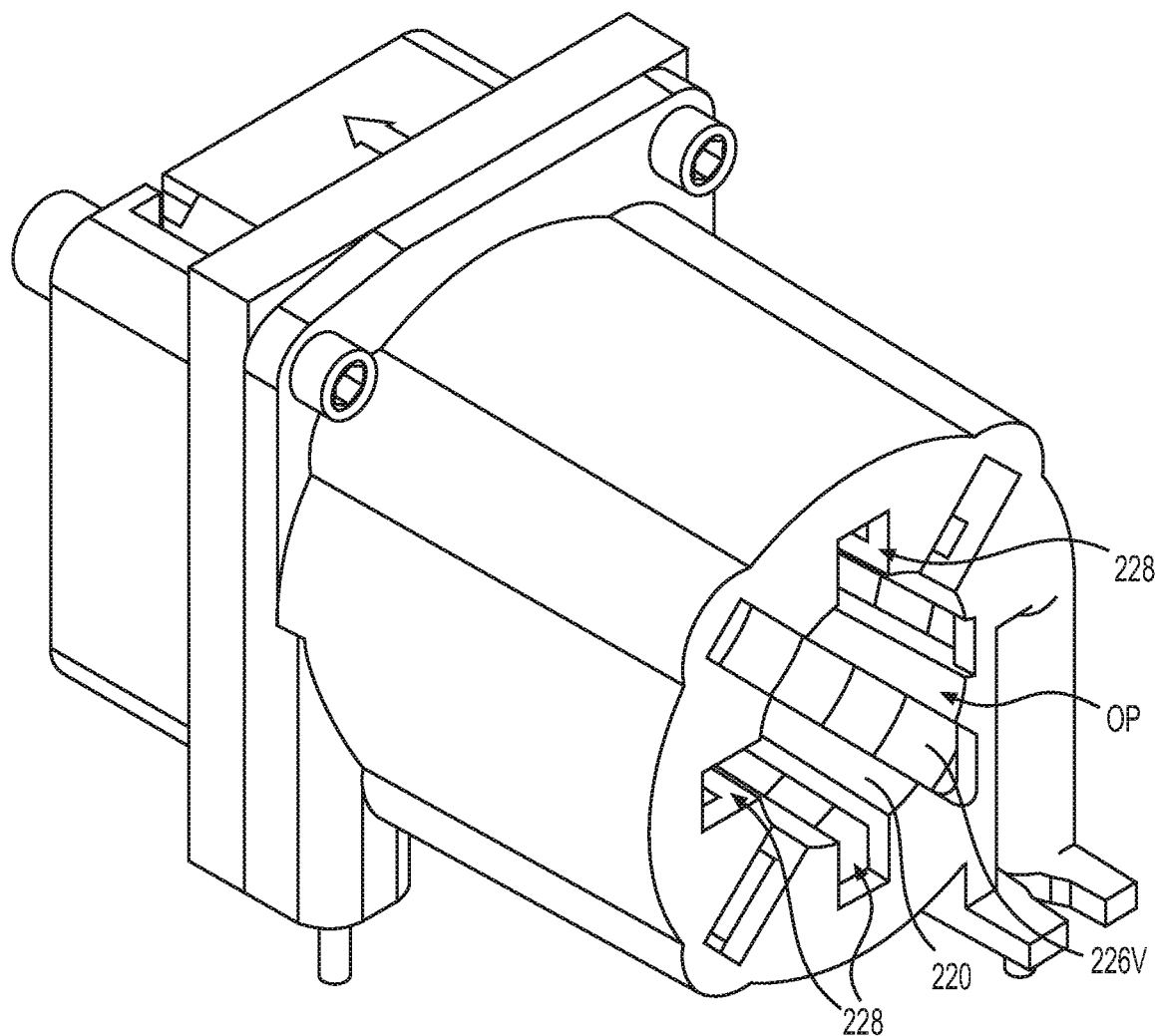
FIG. 4 illustratively depicts another perspective view of the FIG. 2 apparatus, according to the FIG. 3 construct.

FIG. 4 illustratively depicts another perspective view of the gas humidity conditioning 200 apparatus, in the construct shown in FIG. 3, with the housing sidewalls 214 not transparent. Referring to FIG. 4, in an aspect, the winding support 220 introduced in reference to FIG. 2 can be hollow, with an opening OP. The winding support 220 can also have longitudinal slots 228 and, for each, the annular end plate 216 may provide corresponding cutouts or vents (visible in FIG. 4 but not separately labeled). Referring to FIG. 4, portions of the first (starting from the annular end plate 116) three windings of the coiled tube section 226V are visible through three of the longitudinal slots 228, and the corresponding cut-outs or vents formed in the annular end plate 216.

Figure 5A:
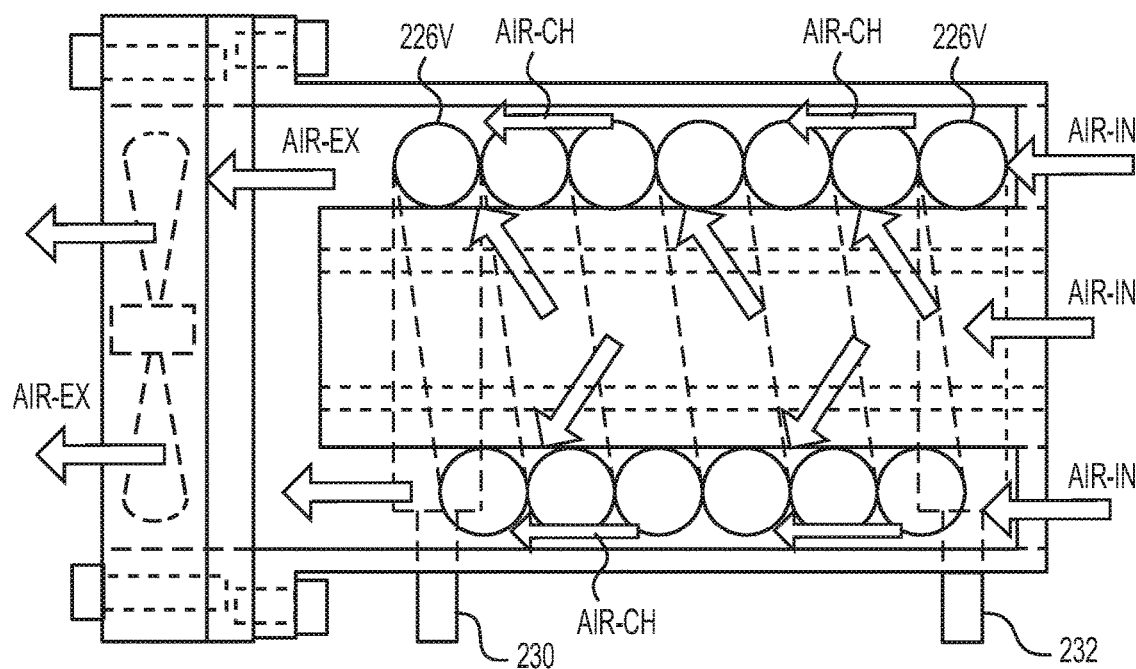
FIG. 5A illustrates a partial cross-sectional view of the construct of FIGS. 2 and 3, cut down a centerline thereof.
Figure 5B:
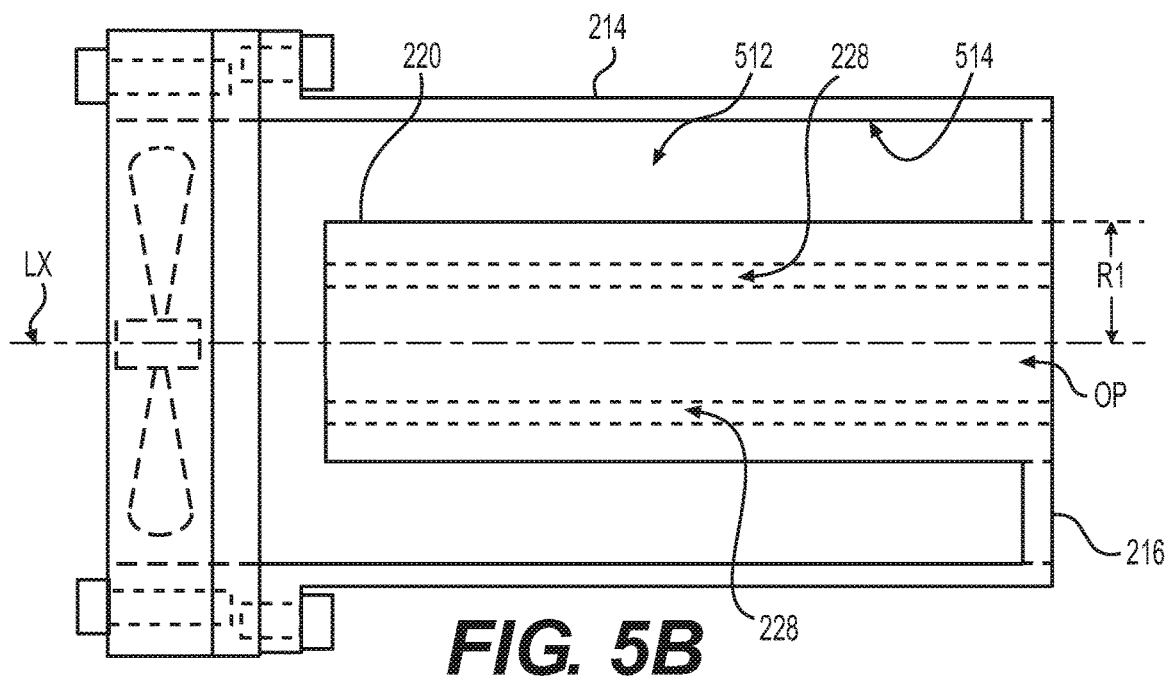
FIG. 5B illustrates the FIG. 5A partial cross-section view, with its exemplary ventilated coiled tube structure removed, to provide additional view of various structures in accordance with one or more aspects.

FIG. 5A illustrates a partial cross-section view of the FIGS. 3 and 4 construct, seen from a cut-through plane containing the winding axis LX. FIG. 5B illustrates the FIG. 5A partial cross-section view, with its exemplary ventilated coiled tube structure removed, to provide additional view of various structures in accordance with one or more aspects.

Referring to FIGS. 5A and 5B, the winding support 220 can be configured to support the coiled tube section coil 226V in a winding configuration having a winding radius R1 from winding axis LX. The coiled tube section 226V can be wound around a support surface (not visible in FIG. 3) of the winding support 220. The support surface of the winding support 220 can be circumferential around and spaced from the winding axis LX by a winding radius R1 or the coiled tube section 226V. Inner surfaces 514 (labeled in FIG. 5B) of the housing sidewalls 214 can be spaced from the coil winding outer surface. The inner surfaces of the housing sidewalls 514 and the support surface of the winding support 220 can define an annular volume, which can accommodate the coiled tube section 226V.

As identified in reference to FIG. 4, and as further visible in FIGS. 5A and 5B, the winding support 220 can have longitudinal slots 228 and, for each of such slots 228, the annular end plate 216 may provide corresponding cutouts or vents (visible in FIG. 4 but not separately labeled).

Referring to FIGS. 4, 5A and 5B, example operations of the gas humidity conditioning apparatus 200 according to various aspects will now be described. Upon powering the fan 222, a negative pressure may be induced in portions of the annular volume 512 that remain after inclusion of the coiled tube section 226V. This pressure can urge ambient airflow AIR-IN to enter that annular volume 512, through the longitudinal slots 228 in the winding support 220, and through corresponding cutouts or vents formed in the annular end plate 216. AIR-IN can urge ambient airflow AIR-CH, which flows over and around the coiled tube section 226V, and then out as AIR-EX through the fan 222.

It will be understood that the combination of the coiled tube section 226V being wound in the annular volume 512, around the winding support 220, which can be hollow with longitudinal slots 228, can maintain the coiled tube section 226V as effectively bathed in the ambient airflow. In an aspect, an outer texture of the sample gas tube 226 forming the coiled tube section. This arrangement, in turn, can establish the coiled tube section 226V as a ventilated tube section 226V. Benefits and features of the ambient airflow AIR-CH bathing the ventilated tube section 226V can include, for example, prevention or significant retardation of any formation of a skin of dry gas around its outer surface. In addition, based in part on the aspect of providing a multiple turn coiled (hence longer) ventilated tube, disclosed aspects can deliver a sample gas with acceptable humidity, for at least a range of extremes of humidity, together with extended useful functional life of the tube.

In the above-described implementations with an air input path and flow though the chamber to an air egress path, the structures functioning as the "input air input path" and "air egress path" are only one example. For example, referring to FIG. 4, in the humidity conditioning apparatus 200 the fan 222 can be reversed. The reversal can change the end of the housing proximal to the housing end flange 218 to an "air input path," and can change the longitudinal slots 228, and corresponding cut-outs or vents formed in the annular end plate 216 to an air egress path. In addition, the fan 222 having its rotational axis collinear and parallel with the winding axis LX is only one example implementation of a fan to urge the described ambient airflow. In one alternative implementation, fan 222 can be replaced with a fan rotated 90 degrees (not visible in the figures) from fan 222, in combination with a 90-degree elbow. In another alternative implementation, fan 222 can be replaced by a radial fan.

According to various aspects, the gas humidity conditioning apparatus 200 (as well as the apparatus 100) may be used with sample gas from a patient breathing apparatus. In some cases the ambient air may be approximately 20 degrees C. and 30% relative humidity, such as for example in health care facilities based on ANSI/ASHRAE/ASHE standard 170-2008: class B and class C operating rooms, recovery rooms, critical and intensive care rooms, newborn intensive care rooms, patient rooms and/or newborn nursery suites. In such situations and others, improved performance and extended service life may have significant value.

Figure 6:
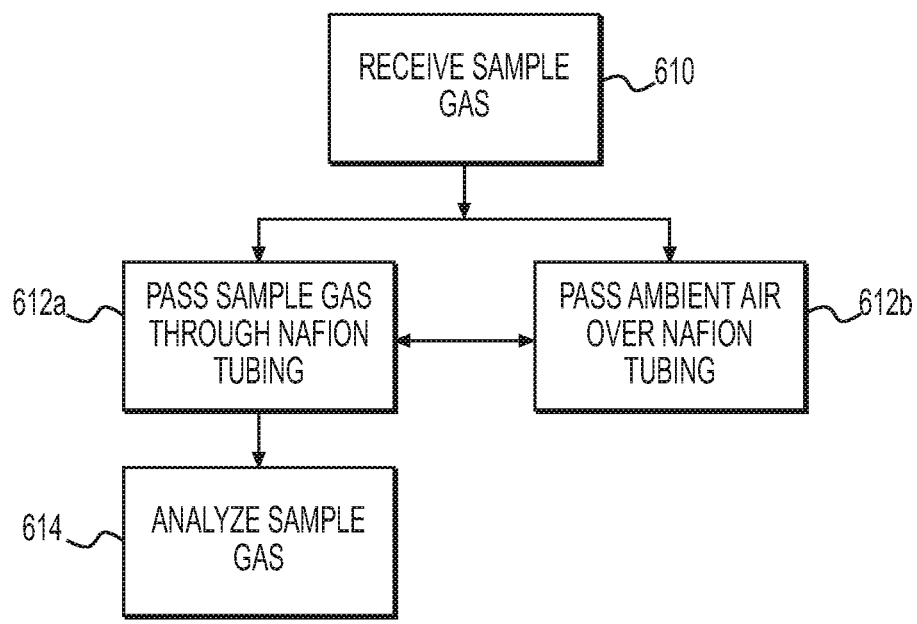
FIG. 6 illustratively depicts one flow diagram, representing example operations in a method directed to humidity conditioning and to extending humidity conditioning tube life, and to other features, in accordance with various aspect.

FIG. 6 illustratively depicts an exemplary flow diagram of an exemplary method for conditioning of sample gas, using an apparatus as described herein. At process 610, sample gas is received, such as the FIG. 1 inlet 130. This sample gas may be taken from a patient breathing gas apparatus, and for example may be from a fitting off an inspiratory limb. At process 612a, the sample gas is passed through Nafion tubing, which may be configured with a ventilated coil section, such as the FIG. 1 ventilated coil section 126V or the FIG. 2 ventilated coil section 226V. Concurrently with process 612a, at process 612b ambient airflow contacts and passes over and around the ventilated coil section 126V (or 226V). The ambient airflow may be, for example, the FIG. 1 or FIG. 5A AIR-CH, and can be urged by a fan, such as the FIG. 1 fan 120 or the FIG. 2 fan 222. At process 614, the sample breathing gas passes out of the Nafion tubing, and is analyzed by a gas analyzer such as described herein and below.

Figure 7:
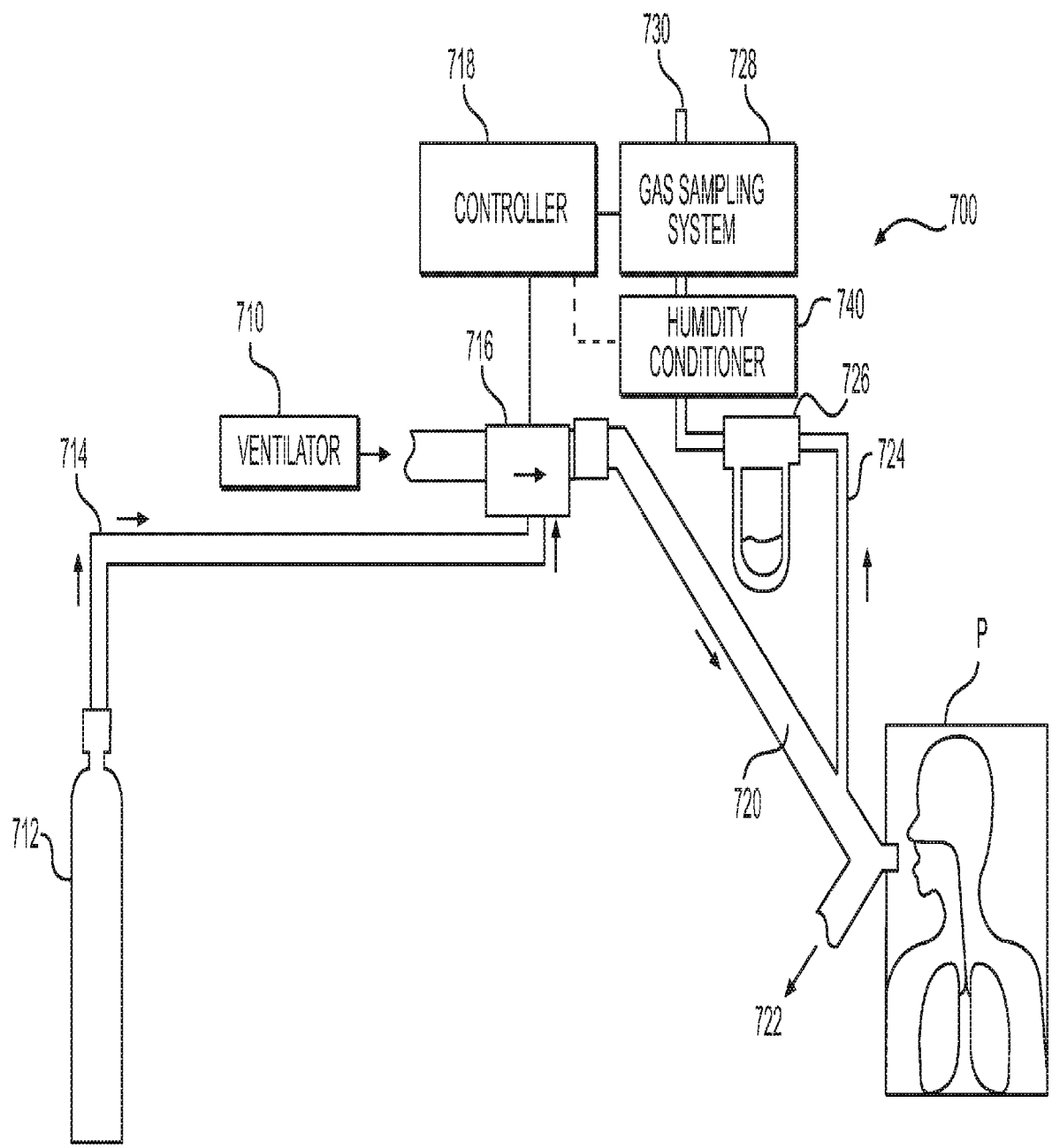
FIG. 7 illustratively depicts at least some aspects of implementation of a Nafion tubing enhancing apparatus, in conjunction with a breathing gas supply apparatus, in accordance with various exemplary aspects of the present disclosure.

FIG. 7 illustratively depicts some aspects of exemplary implementations of exemplary gas conditioners as described herein, in conjunction with a breathing gas supply apparatus. An apparatus 700 is used with a ventilator 710. A supply 712 of supplemental or additive gas such as NO provides a supply to conduit 714 and leads to a flow sensor 716 which may also be connected to the ventilator 710. At any stage of breathing gas supply, other additional breathing materials such as nebulized drugs may be provided into a stream that travels via conduit 720. A controller 718 may actuate valves to control, for example, the ratio of NO to the mixture gas in conduit 720. A patient inhales the content of conduit 720 which may be considered as an inspiratory limb. The patients exhale or excess gas may be considered as an expiratory limb conduit 722. While the sample gas is illustrated in this implementation as being drawn from the inspiratory limb 720, it may be drawn from other parts of the patent breathing apparatus.

In this example, a conduit 724 is in fluid communication with the inspiratory limb and may be referred to as a sample gas line. A filter trap 726 receives some or all of the sample gas. This filter trap 726 may correspond to a filter assembly that removes water and/or particulates from the sample gas. After being filtered by the filter trap 726, the gas is passed to a gas conditioner apparatus labeled 740. In an aspect, the gas conditioner apparatus 740 can be, for example the humidity conditioning apparatus 100 described in reference to FIG. 1, or the gas sample humidity conditioning apparatus 200 described in reference to FIGS. 2-5B. After leaving the gas conditioner apparatus 740, the now humidity-conditioned sample gas can pass to a gas sampling system 728, and may exhaust via exhaust outlet 730. In some implementations, the controller 718 may control some operations of the conditioner apparatus (100, 200, 740) such as by way of example only, the fan speed thereof.

The foregoing detailed descriptions are presented to enable any person skilled in the art to make and use the disclosed subject matter. For purposes of explanation, specific nomenclature is set forth to provide a thorough understanding. However, it will be apparent to one skilled in the art that these specific details are not required to practice the disclosed subject matter. Descriptions of specific applications are provided only as representative examples. Various modifications to the disclosed implementations will be readily apparent to one skilled in the art, and the general principles defined herein may be applied to other implementations and applications without departing from the scope of this disclosure. The sequences of operations described herein are merely examples, and the sequences of operations are not limited to those set forth herein, but may be changed as will be apparent to one of ordinary skill in the art, with the exception of operations necessarily occurring in a certain order. Also, description of functions and constructions that are well known to one of ordinary skill may be omitted for increased clarity and conciseness. This disclosure is not intended to be limited to the implementations shown, but is to be accorded the widest possible scope consistent with the principles and features disclosed herein.

It will be apparent to those skilled in the art that various modifications and variations can be made to the methods and systems of the present description without departing from the spirit and scope of the description. Thus, it is intended that the present description include modifications and variations that are within the scope of the appended claims and their equivalents.

It will be understood that any of the steps described can be rearranged, separated, and/or combined without deviating from the scope of the invention. For ease, steps are, at times, presented sequentially. This is merely for ease and is in no way meant to be a limitation. Further, it will be understood that any of the elements and/or embodiments of the invention described can be rearranged, separated, and/or combined without deviating from the scope of the invention. For ease, various elements are described, at times, separately. This is merely for ease and is in no way meant to be a limitation.

The separation of various system components in the examples described above should not be understood as requiring such separation in all examples, and it should be understood that the described components and systems can generally be integrated together in a single package into multiple systems and/or multiple components. It is understood that various modifications may be made therein and that the subject matter disclosed herein may be implemented in various forms and examples, and that the teachings may be applied in numerous applications, only some of which have been described herein. Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

Although the invention herein has been described with reference to particular implementations, it is to be understood that these are merely illustrative, to further assist persons of ordinary skill in understanding the present concepts to make and use embodiments thereof. It will also be apparent to such persons, upon reading this disclosure in its entirety that various modifications and variations can be made to the methods and apparatus as disclosed without departing from the spirit and scope of the invention. Thus, it is intended that the present invention include modifications and variations that are within the scope of the appended claims and their equivalents.

What is claimed is:

1. A sample gas conditioning apparatus, comprising:
    a housing, at least partially defining a chamber, and at least partially defining an air input path into the chamber and an air egress path from the chamber, the housing comprising:
        an annular end plate comprising:
            an inner perimeter edge that is spaced from and circumferential around a winding axis;
            an outer perimeter edge; and
            a winding support extending from the inner perimeter edge, a support length toward a housing open end; and
        housing side walls that extend from the outer a peripheral rim region to the housing open end, in a direction parallel to the winding axis;
    a fan, connected to the housing, configured to urge an ambient air flow through the chamber, the ambient air flow entering through the air input path into the chamber, and exiting the chamber through the air egress path;
    a sample gas tube having a coiled tube section that comprises a water permeable material, at least a portion of the coiled tube section being arranged in the chamber as a ventilated section, the ventilated section being ventilated by the ambient air flow through the chamber, wherein the coiled tube section comprises a coil winding around the winding axis and the winding support,
    wherein the fan, the air input path, the air egress path, and the housing have a joint configuration that urge the ambient air flow through the chamber to have a flow direction, the flow direction being generally parallel to the winding axis.

2. The sample gas conditioning apparatus of claim 1, wherein the fan, the housing and the ventilated section have a joint configuration that establishes the ambient air flow through the chamber with a flow that prevents or significantly retards formation of a skin of dry gas around an outer surface of the ventilated section.

3. The sample gas conditioning apparatus of claim 2, wherein the sample gas tube has an input end and an output end, wherein the ventilated section provides a passage for a sample gas, the passage having a passage length, wherein the passage length in combination with a flow rate of the sample gas provides, for at least a range of humidity level at the input end that is outside of a desired range, a humidity of the sample gas at the output end that is within the desired range.

4. The sample gas conditioning apparatus of claim 3, wherein the desired range extends from approximately 15% relative humidity to approximately 90% relative humidity.

5. The sample gas conditioning apparatus of claim 1, wherein the sample gas tube has an input and an output, wherein the sample gas conditioning apparatus further comprises a connection of the input to a conduit, wherein the conduit is configured to deliver a mixture of a mixture gas and a therapeutic gas to a patient, and wherein the sample gas tube is configured to provide passage of a sample of the mixture of the mixture gas and the therapeutic gas to the ventilated section, and to output, at the output, a humidity conditioned sample of the mixture of the mixture gas and the therapeutic gas, wherein the therapeutic gas comprises nitric oxide.

6. The sample gas conditioning apparatus of claim 1, wherein the water permeable material comprises a sulfonated tetrafluoroethylene based fluoropolymer-copolymer.

7. The sample gas conditioning apparatus of claim 1, wherein the water permeable material comprises Nafion.

8. The sample gas conditioning apparatus of claim 1, wherein the ventilated section provides a ventilated tubular membrane formed of the water permeable material, and the water permeable material transfers humidity through the ventilated tubular membrane, based on First Order Kinetic reaction.

9. The sample gas conditioning apparatus of claim 8, wherein the ventilated tubular membrane has a start and an end, and provides a passage length from the start to the end, wherein based at least in part on the passage length the ventilated tubular membrane provides, for at least a range of humidity level of a sample gas at the start that is outside of a given acceptable range, a humidity level of the sample gas at the end that is within the given acceptable range.

10. The sample gas conditioning apparatus of claim 1, wherein the coiled tube section consists of at least two coil turns.

11. The sample gas conditioning apparatus of claim 1, wherein the coil is a coil winding among a plurality of coil windings.

12. The sample gas conditioning apparatus of claim 1, wherein the coil winding forms a coil winding outer surface, the coil winding outer surface being radially distal from the winding axis, wherein the chamber is defined, at least in part, by an inner surface of the housing that extends a length along the winding axis and, circumferentially around the winding axis, faces toward the winding axis.

13. The sample gas conditioning apparatus of claim 1, wherein the winding support is configured to support the coil winding in a winding configuration having a winding radius, the winding radius extending radially from the winding axis.

14. The sample gas conditioning apparatus of claim 13, wherein an inner surface of the housing side walls faces toward the winding axis, circumferentially around the winding axis, wherein the inner surface of the housing side walls and the winding radius define an annular volume within the chamber, centered around the winding axis, that extends from the annular end plate toward the housing open end.

15. The sample gas conditioning apparatus of claim 14, wherein the winding support comprises a hollow structure, having longitudinal slots, configured to provide for ingress of the ambient air into the annular volume.

16. A sample gas conditioning system comprising:
a housing, at least partially defining a chamber, and at least partially defining an air input path into the chamber and an air egress path from the chamber;
a fan, connected to the housing, configured to urge an ambient air flow through the chamber, the ambient air flow entering through the air input path into the chamber, and exiting the chamber through the air egress path; and
a sample gas tube, having a section that comprises a permeable material, at least a portion of the section being arranged in the chamber as a ventilated section, the ventilated section being ventilated by the ambient air flow through the chamber and including a coiled tube section comprising a coil winding around a winding axis,
wherein the housing includes a housing cap, having a cap perimeter, and includes housing side walls that extend from the cap perimeter to a housing open end, parallel to the winding axis, wherein an inner surface of the housing side walls faces and has a clearance from an outer surface of the coil winding, wherein the housing open end has a housing open end area, wherein the air egress path includes at least a portion of the housing open end area.

17. The sample gas conditioning system of claim 16, wherein the housing cap is a vented housing cap, providing a vent into the chamber, wherein the air input path comprises the vent.

18. The sample gas conditioning system of claim 16, wherein the fan comprises an electric motor, supported in a fan housing, having a rotor shaft and a rotary fan blade attached to the rotor shaft,
wherein the housing includes a housing mounting flange at the housing open end, and
wherein the fan housing is secured to the housing mounting flange, in a configuration wherein the rotor shaft is parallel to the winding axis.

19. The sample gas conditioning system of claim 18, wherein the fan housing is secured to the housing mounting flange by an adapter plate, the adapter plate having an adapter plate first face and, opposite and parallel to the adapter plate first face, an adapter plate second face, wherein the fan housing is secured, by fan housing mount bolts, to the adapter plate first face, wherein the housing mounting flange is secured, by housing mount bolts, to the adapter plate second face.

* * * * *